United States Patent [19]

Conrad

[11] Patent Number: 5,032,292

[45] Date of Patent: Jul. 16, 1991

[54] METHOD FOR PREVENTING BIOFILM IN SPAS

[76] Inventor: Richard H. Conrad, 950 Idylberry Rd., San Rafael, Calif. 94903

[21] Appl. No.: 514,159

[22] Filed: Apr. 25, 1990

[51] Int. Cl.[5] .............................. C02F 1/50; C02F 1/78
[52] U.S. Cl. ..................................... 210/764; 210/760; 210/169; 210/136; 4/544; 128/66
[58] Field of Search ............... 210/760, 169, 758, 136, 210/205, 764; 4/541, 542, 543, 544; 128/65, 66, 369

[56] References Cited

U.S. PATENT DOCUMENTS 3,441,015  4/1969  Oatman et al. ........................ 4/544
4,563,781  1/1986  James .................................... 4/544

Primary Examiner—Stanley Silverman
Assistant Examiner—Neil M. McCarthy
Attorney, Agent, or Firm—Larry D. Johnson

[57] ABSTRACT

A method for preventing stagnation and biofilm formation in the jet pump circuit of a spa, therapy pool or bath employing separate pumps or plumbing circuits for circulation and for pressure jet/massaging functions. The method includes a bidirectional water conduit through which water flows in one direction when the circulation pump is on, and in the other direction when the jet pump is on. All plumbing in the jet pump circuit is thereby kept free of biofilm by causing water containing a dissolved disinfectant to flow through it while the circulation pump is on. The invention further includes methods for automatically flushing the massage jet air lines and the air bubbler chamber with disinfectant-containing water while the circulation pump is on. This method increases the reliability and safety of spa disinfection, reduces the quantity of disinfectant needed, and in some cases enables ozone to be used as the major or sole disinfectant.

9 Claims, 7 Drawing Sheets

METHOD FOR PREVENTING BIOFILM IN SPAS

BACKGROUND OF THE INVENTION

1. Field of the Invention

This invention relates generally to spas, hot tubs, therapy baths and the like, and more specifically to methods for preventing stagnation and biofilm formation in such systems.

2. Description of the Prior Art

A major goal in the design of spas should be that they be as hygenic as possible. This goal has not been realized in the prior art because the spa has not been viewed as the potential bacteriological incubation chamber that it actually is. Disinfection involves hydrodynamic and mechanical as well as chemical factors and should be based on microbiological principles, including avoiding the creation of areas where water can lie stagnant in dead-ended pipes or blind chambers, and consideration of the tendency of bacteria to form biofilms. These principles have not been primary design considerations in the prior art. Stagnant areas act in a manner analogous to the human appendix, culturing and harboring high concentrations of bacteria. The bacteria often adhere to even well-flushed pipelines in spas and secrete a gel-like protective layer of exopolysaccharides which makes them highly resistant to disinfection. These protected cultures, commonly called biofilms, continuously shed bacteria into the water and re-innoculate the spa. They are reservoirs of potentially pathogenic bacteria which are not killed by concentrations of chlorine that are adequate to disinfect the water itself (J. W. Costerton and H. M. Lappin-Scott, ASM (American Society for Microbiology) News, Vol. 55, No. 12, pp. 650-654, 1989). These bacteria can reach the bather when they adhere to floating particles in the water which protect them from disinfection and/or when free halogen levels transiently dip below 1 part per million (in the case of chlorine). In addition, contrary to popular assumption, chlorine takes minutes rather than seconds to kill most bacteria and one-celled parasites.

Spa plumbing design should be brought up to good standards from a microbiological viewpoint, because a heated spa is truly such a potential culture medium. It is a veritable fermentation tank. Four persons sitting in the average 400 gallon spa is equivalent to 100 gallons/person, which is the same as having 200 people all at once in a small residential swimming pool of 20,000 gallons. But the situation is actually even much worse than that because in the hot water of the spa, far more perspiration, oils and flakes come off the skin. Furthermore, public spas typically containing about 1,000 gallons of water and often over 100 feet of piping are used by dozens and sometimes hundreds of people every day, with the water being changed anywhere from once every 24 hours to once a week. In private spas, commonly used by a few people daily, the water is generally changed only once every two to three months.

It takes a minimum concentration of at least 1 ppm (part per million) of free chlorine or 2 ppm of free bromine to keep the spa water safely disinfected, a higher ppm to reliably prevent a growth of biofilm on the inside of the pipes, and again a yet even higher ppm to reverse any biofilm growth which may have occured during a short-term dip in disinfectant concentration. Biofilm is often composed of either Pseudomonas or Corynebacterium, both of which can be pathogenic. Dozens of research papers have been published on outbreaks of various skin, urinary, ear and other infections caused by bathing in infected spas (see E. W. Mood, Proceedings, Ninth Ozone World Congress, N.Y., 1989, pp. 382-387; and also P. H. Chandrasekar et al., Archives of Dermatology, Vol. 120 No. 10, 1984, pp. 1337-1340). Biofilms tend to form on both smooth and rough surfaces, inside of filters and on filter components, and are found as up to 1/16" thick coatings of gel or slime lining the inside of the PVC "flex" hose commonly used in spa construction. When water flows through a pipe lined with biofilm, many bacteria are shed into the flow and quickly reach the tub. In repeated experiments beginning with a completely disinfected tub, the effluent of the circulation circuit where it re-enters the tub was found to contain 8,000 to 10,000 bacteria per ml. with the filter in the circuit, and 2,000 to 6,000 bacteria per ml. when the filter was bypassed. Biofilms can significantly reduce the usable diameter of the pipes, thus reducing flow rates and making pumps work harder. Biofilm formation is enhanced by warm temperatures, stagnation, and by organic nutrients in the water. Prior art disinfection strategy has been directed towards killing free-floating bacteria. The awareness of the importance of biofilms requires new disinfection perspectives and methods. The present invention provides such methods, where water containing a disinfectant is caused to flow through the jet pump circuit while the circulation pump is on. The cleanest pipe surfaces result when the disinfectant is ozone or at least includes ozone, not only because biofilm bacteria are more sensitive to ozone than they are to chlorine, but also because ozone oxidizes organic materials both adhering to the pipes and dissolved in the water, thus reducing the level of organic nutrients for bacteria to grow on.

In both public and private spa installations it is very common to employ dual pump or dual-speed single-pump plumbing systems, with a low speed pump being used for circulation, filtering, and heating (and ozonation, where used) and the high speed for pressure-jet/massaging functions. During intervals when the jet pump is not used, overnight, for example, the concentration of disinfectant in the jet pump plumbing loop can drop to near zero in spite of the fact that a circulation pump and automatic chlorine feeder maintain a "safe" disinfectant concentration in the circulation circuit and in the tub. Biofilm itself consumes disinfectants, contributing to a rapid decrease of disinfectant concentration in stagnant loops. This allows the growth or regrowth of a biofilm lining on the inside of the pipes of the jet pump plumbing circuit, and bacterial growth in the water contained within these pipes, which then re-innoculate the spa whenever the jet pump is turned on. This serious problem becomes even more critical in spas which utilize ozone as a major or sole disinfectant, because an ozone residual lasts only minutes in stagnant areas and because in "ozone only" systems it is highly advantageous to employ a dual speed type of system, with separate pumps (or separate speeds with a dual-speed pump) and at least partially separate piping loops for circulation/filtration/heating/ozonation and for pressure-jet/massaging functions, as will be described below.

The problems of stagnation and biofilm formation in spas have not been satisfactorily dealt with in the prior art, and the methods of the present invention solve these problems. The use of the methods of the present invention make any disinfectant more effective, producing more thorough, reliable disinfection while using up less disinfectant. In addition, the methods of this invention become a necessity for sucessful use of ozone as the sole disinfectant.

Chlorine is the most commonly used disinfectant. Adequate disinfection of free-floating bacteria is generally obtained at concentrations of free chlorine above 1 ppm. But since chlorine is a biological poison, at these concentrations, especially in warm water, it can cause bathers to have dry, scaly itching skin; dry, brittle bleached hair; and various allergic reactions, as well as having an unpleasant smell both in the warm vapors rising from the water surface and on the skin and hair afterwards. In addition, when chlorine reacts with by-products from the bathers' skin (both after they are shed into the water and also on the skin itself) it forms chloramine compounds which are approximately fifty times more irritating (especially to the eyes) and smell much more strongly than chlorine. Even worse than the chloramines are the similarly formed trihalomethanes or "THM's", which are universally accepted as being human carcinogens. THM's have been shown to be absorbable through human skin into the bloodstream, particularly from hot water (H. S. Brown, D. R. Bishop and C. A. Rowan, Am. J. of Public Health, May 1974, Vol. 74 No. 5, pp. 479–484). Bromine, also widely used in spas, has been reported to be worse than chlorine as far as skin hyper-sensitization reactions are concerned, and also because it forms carcinogenic bromoforms which are volatile and are released into the air at the surface of the spa.

Chlorine and bromine are "residual-type" disinfectants, that is, they have a relatively long lifetime in the water. On the other hand, ozone (O3), which is a far more powerful disinfectant and oxidant than either chlorine or bromine, has a rather short lifetime in water, particularly in hot water, disinfects between 10 to 3000 times faster than chlorine, does not produce toxic by-products (P. M. Huck, et al., Ozone Science and Engineering, Vol. 11, No. 3, pp. 245–269), oxidizes many of the compounds secreted by the bathers' skin, has a microflocculation action which produces very clear water, and reverts back to oxygen. It does its job and then disappears, and would leave the water disinfected, clean, and clear, if it could be applied properly. Ozone cannot be used by itself in public spas because in public spas a residual disinfectant is required by law, and ozone provides very little residual concentration in the tub itself. But if enough ozone is used properly in addition to chlorine, it will prevent the formation of most of the irritating and dangerous chlorine byproducts. (When bromine is used it is difficult for ozone to prevent the formation of bromoforms. For this purpose a much higher concentration of ozone is required, together with the addition of a flocculant (D. Pacik and R. G. Rice, Proceedings, Ninth Ozone World Congress, N.Y., 1989, pp. 419–443).)

If properly applied, ozone could be used in private spas alone, without a residual disinfectant in the water of the tub itself, to provide clear, sterile, sweet-smelling hot water for the bather. Additional reasons that it would be highly desirable to be able to operate private spas on ozone alone are that ozone is generated electrically on site from air as needed and no purchasing, transporting, storing, handling, or manual dosing is necessary as it is with the halogens, and ozone does not affect the pH so that most of the handling, etc, of acids or bases is not required as it is with the halogens (which cause pH imbalance and continually require the concommitant addition of acid or base). When properly applied with an ozone reaction tank which provides adequate contact time and with provision for adequate off-gassing and off-gas destruction before the water returns to the spa, there should be either very little or no ozone detectable in the air above the surface of the spa (which is the condition desired in order to prevent the release of ozone into the atmosphere and to avoid contact with the lungs). Thus in a private spa ozone could eliminate chemicals and much of the maintanence, make completely automatic spa operation very easy to implement, and cause spa usage to be more healthy and pleasant because of the purity of the water. As the repeated use of the words "would" and "could" in this and the previous paragraph imply, the ability to safely use ozone as the sole disinfectant in even private spas has not yet been realized in the prior art. This is because of biofilm growth in the jet pump circuit and/or bubbler chamber. This problem, and its solution by the method of the present invention, will be described below.

The concentration of ozone commonly supplied by the ultra-violet ozone generators commonly used on spas is usually insufficient to actually destroy any substantial numbers of bacteria, and has little effect on Giardia, Cryptosporidium, amoebic cysts, or on biofilm formation in pipelines. In these rather low concentrations usually used, ozone acts merely as a clarifier, causing enough oxidation and microflocculation to maintain turbidity at very low levels. This misleads people to believe, and advertisers to advertise, that generally if ozone is used in a spa and it keeps the water clear and the smell of ozone is detectable, that it is also disinfecting the spa and the spa may therefore be safely used without a residual disinfectant such as chlorine or bromine. This has been shown to be a dangerously mistaken assumption, by both G. E. Whitby in his article: "The treatment of Spa Water With Ozone Produced by UV Light" published in Ozone Science and Engineering, Vol. 11, No 3, pp. 313–324, 1989, and by my own bacteriological testing and research. For example, the water in toilet bowls usually looks quite clear, but that doesn't mean it is sterile. Ozone itself can disinfect completely, but only if applied in the proper manner and in adequate quantity and concentration, such as can be generated by corona discharge techniques.

For ozone used alone to be effective for disinfection, oxidation and biofilm prevention as well as for clarification purposes, it is necessary to circulate the spa water through an ozone injector and ozone contacting/reaction volume (tank, piping, chamber, etc.) either continuously or at frequent intervals (for example for one hour every 4 to 6 hours) with the injection of at least 0.5 gram/hour of ozone of at least 1.0% concentration for every 1,000 gallons per hour (or 17 GPM) flow rate of water, with a water turnover rate of preferably 20 minutes or less. Under these conditions the pipes and flex hoses downstream of the ozone injection point remain "squeaky clean", and when a test section of PVC flex hose containing a 1/16" thick coating of biofilm (which took many weeks to grow) was inserted 45 seconds downstream of this point, the section became clean after about 6 hours of ozonation.

By the time ozonated water travels from the point of ozone injection, through the ozone reaction volume and back into the spa, it is sterile. By the time the water leaves the spa again the concentration of ozone is much less than it was at the point of injection because the half-life of ozone in water at spa temperatures is on the order of only a few minutes (which is the situation desired in order to avoid exposing bathers to significant concentrations of ozone in the water or in the air). Because of the low concentration of ozone leaving the spa, some biofilm will form between the suction drain/exit from the spa and the point of ozone injection, but any bacteria shed from this film will be completely destroyed by the freshly injected ozone before the water returns to the spa. It is very impractical to try to prevent the formation of biofilm before the point of ozone injection by a direct recirculation means, because this would require a direct recirculation of at least half of the ozone containing-water in order to avoid too much dilution of the ozone, which dictates doubling the pump and ozonator size and power usage and also requires that all components, including circulation pump, filter and heater be ozone resistant. Biofilm does not usually form on the slick acrylic walls of the inside of the tub itself, and lightly wiping the underwater surfaces and waterline with the bare hand once a week is generally adequate to keep them clean (except in halogenated spas, which form a yellow, greasy, chemically-smelling scum at the waterline which is difficult to remove).

In almost all spa installations, a high volume, high pressure pumping speed is required to activate the therapeutic pressure jets. This high speed and volume is not suitable for use while injecting ozone or circulating ozonated water. This is because an ozonation pump must be on for 4 or more hours/day (preferably at spaced intervals, e.g., on for 1 hour and off 4 hours, etc.) and at a modest flow rate so that a reasonably sized ozone generator can maintain the required dissolved ozone concentration and so that a substantial (0.5 to 2 minutes) contact time for reaction of the dissolved ozone with the water can be achieved without requiring an overly large contact volume (tank), and also because a high speed pump would be expensive in power usage and noisy to operate 4 or more hours/day. Thus for efficient, practical operation, a spa system using ozone as the sole or major disinfectant must employ either a dual-speed pump, or a circulation/ozonation pump plus a separate higher speed jet pump.

The very serious problem that still remains in applying ozone technology to spas, a problem that the method of the present invention addresses and solves completely, is that although the circulation/ozonation pump can keep its own plumbing circuit free of biofilm (at least downstream of ozone injection), it does not in the prior art keep biofilm from growing in the jet pump plumbing circuit nor in an air bubbler chamber.

Ozone is not usually injected into the plumbing of a jet pump circuit during jet pump operation. This would be undesirable because of the ozone outgassing that would then occur in the tub itself, nor would it kill shedded biofilm unless the size (and cost) of the ozone generator and contact tank were increased to match the higher flow rate of the jet pump (about a 3-fold increase). Therefore biofilm will form in the prior art jet pump circuit (especially in the absence of, and often in spite of an added residual-type disinfectant such as chlorine or bromine). This bacterial growth will be aided and maintained by the fact that, since the jets are normally used only sporadically, the water lying in the jet pump circuit will often be stagnant for long periods of time. Thus when the jet pump is turned on, the tub will be rapidly innoculated with huge quantities of bacteria shed from a freely growing biofilm.

Additionally, in the prior art the air intakes and air lines of the venturi jets in the walls of the tub are usually plumbed in such manner that for most of the time they are filled half with air and half with warm stagnant water, a situation in which bacteria grow rapidly. Even in systems using chlorine, biofilm will thrive in such an environment, innoculating the tub each time the jet pump goes on and the air inlets are open, even if the water coming from the jet pump is sterile.

Furthermore, no disinfection means, neither chlorine, bromine or ozone is completely effective or reliable in spas with dead-ended pipes, blind cavities or the usual types of air bubbler chamber. In particular, the typical air bubbler chamber in many fiberglass/acrylic spas acts as a cavernous appendix and incubation chamber with a large, rough-surfaced, un-wipeable internal surface area encompassing a large inaccessible volume which has no flow-through of water, contains warm trapped air and water, and only occasionally sees an effective concentration of residual disinfectant. It is very often full of all kinds of growths which re-innoculate the tub with such huge quantities of bacteria and other species each time the bubbler is turned on that not even a rather high concentration of chlorine can kill them all before they reach the bather sitting on the spa seat. It would not be desirable to apply gaseous ozone directly within the bubbler chamber because in any effective quantity the ozone would immediately bubble up into the air space above the spa and would exceed safe breathing/atmospheric release limits. This invention teaches a method of keeping a bubbler manifold constructed of pipes safely disinfected, but there is no way to keep the rough-surfaced under-the-seat bubbler chamber common in fiberglass spas safely disinfected, and it would be best if the manufacture of this type were discontinued. (In pre-existing spas with such chambers, the bubbler holes can be individually plugged with epoxy or silicone after being drilled clean with a conical reamer so that the weight of the water cannot push the plug through.)

SUMMARY OF THE INVENTION

This invention comprises a method and apparatus for preventing stagnation and biofilm formation in the hydraulic circuit of a spa, therapy pool or bath in which the hydraulic circuit employs separate pumps or separate plumbing circuits for circulation and for pressure-jet/massaging functions. The novel method includes a bidirectional water conduit through which water flows in one direction when only the circulation pump is on, and in the other direction when the jet pump is on. All plumbing in the jet pump circuit (as well as all plumbing downstream from the point of ozone injection in an "ozone only" system) is thereby kept free of biofilm by causing water containing a dissolved disinfectant to flow through it while the circulation pump is on, thus preventing stagnation and biofilm formation in all plumbing that could shed into the tub, and enabling the water flowing into the tub to be free of added bacteria irrespective of which pump or pump speed is operative. The method further includes similar provisions for automatically flushing the massage jet air lines and the air bubbler chamber and outlets with disinfectant-containing water while the circulation pump is on.

The method of the present invention increases the reliability and safety of spa disinfection, reduces the quantity of disinfectant needed, and in some cases enables ozone to be used as the major or sole disinfectant in private spas. When not in use, spas operating on ozone alone would preferably be kept covered by the commonly employed opaque type of cover in order to prevent the growth of algae in the spa itself. All parts of the method of the present invention are of value not only in private spas operating on ozone alone, but also in any spa utilizing any type of disinfection, either with or without the use of ozone, covered or uncovered, and irrespective of whether they stand alone or share their plumbing, pump, filter, etc. with a swimming pool. The three parts of the method may be applied either all together, or in any combination as desired or as limited by the features of each particular spa.

BRIEF DESCRIPTION OF THE DRAWINGS

FIG. 1a illustrates the circulation pump and the jet pump each having independent intakes from and outlets to the spa; and FIG. 1b illustrates the circulation pump and the jet pump sharing a common intake from and outlet to the spa;

DETAILED DESCRIPTION OF A PREFERRED EMBODIMENT

Figure 1A:
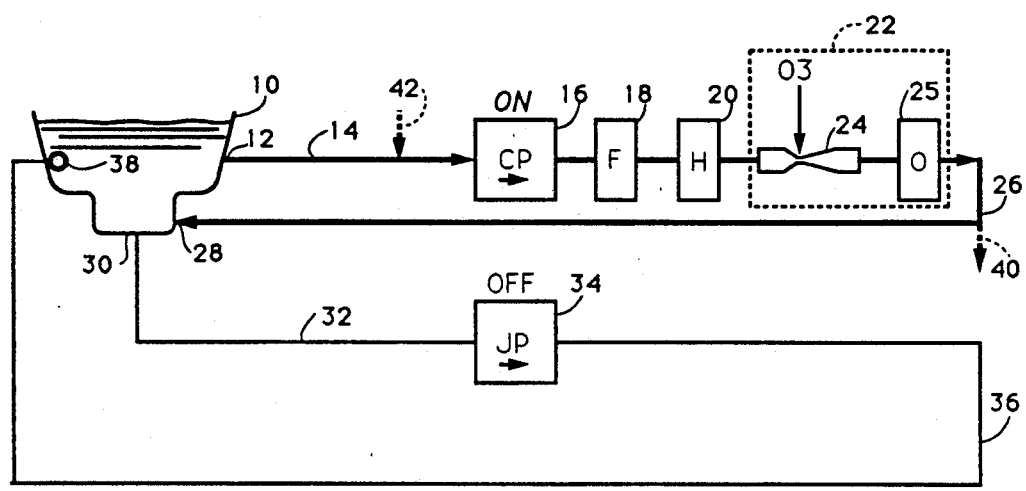
FIGS. 1a and 1b are schematic views of prior art dual pump plumbing systems for a spa or pool, having a first low speed circulation pump for circulation, filtering, and heating; and a second high speed jet pump for pressure-jet and massaging functions.
Figure 1B:
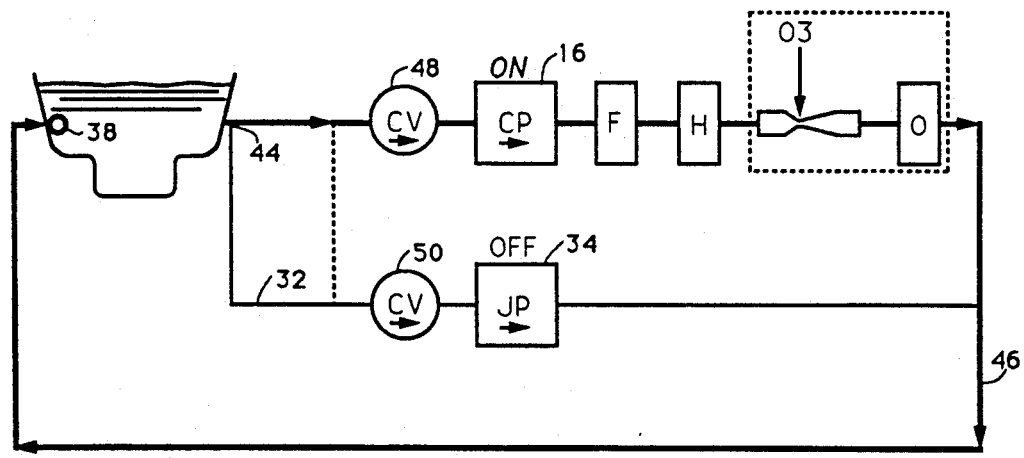

FIGS. 1a and 1b are schematic views of prior art dual pump plumbing systems for a spa or pool, each having a first low speed circulation pump for circulation, filtering, heating and in some cases ozonating; and a second high speed jet pump for pressure-jet and massaging functions. FIG. 1a illustrates a spa or pool 10, a circulation line intake 12, a circulation suction line 14, a circulation pump 16 (also labeled "CP"), a filter 18, a heater 20, a disinfectant source such as an ozone injection device 22 including a venturi 24 and ozone reaction tank 25, a circulation return line 26, a circulation return line outlet 28, a jet line intake 30, a jet suction line 32, a jet pump 34 (also labeled "JP"), a jet return line 36, and a jet return line outlet 38. Optionally, these components may be shared with a separate swimming pool or other tank via an additional outlet line 40 and inlet line 42.

FIG. 1b illustrates a similar system, but with a common circulation line/jet line intake 44 from the spa, and a common circulation/jet return line 46 to the spa. In this prior art system, a circulation line check valve 48 and a jet line check valve 50 are necessary to prevent the flow from bypassing the spa by flowing through a non-operating pump's line.

In both FIG. 1a and FIG. 1b, when the jet pump is off, the water remains stagnant in all portions of the jet pump line not in series with the circulation pump flow. These portions are thus prone to biofilm growth.

Figure 2A:
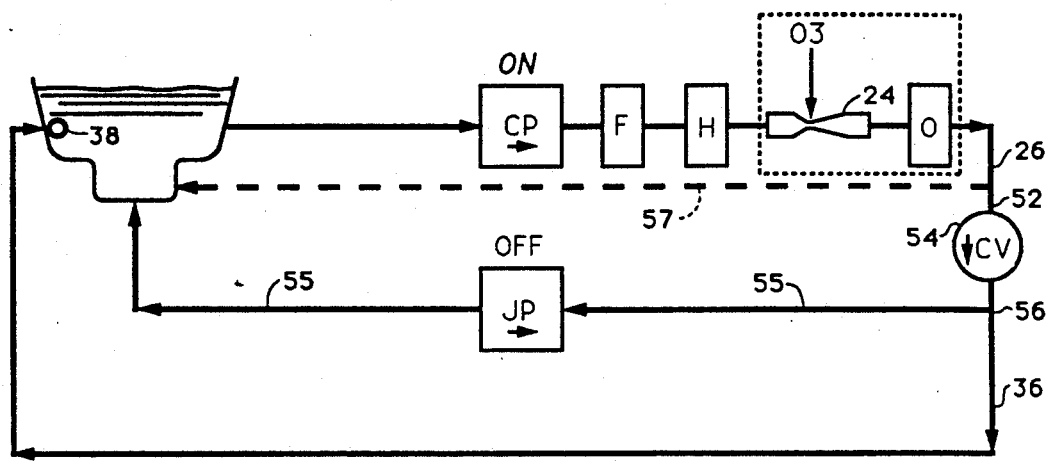
FIGS. 2a-2c are schematic views of a preferred embodiment of this invention, with a bidirectional water conduit creating reverse flow through the jet pump and jet pump line.
Figure 2B:
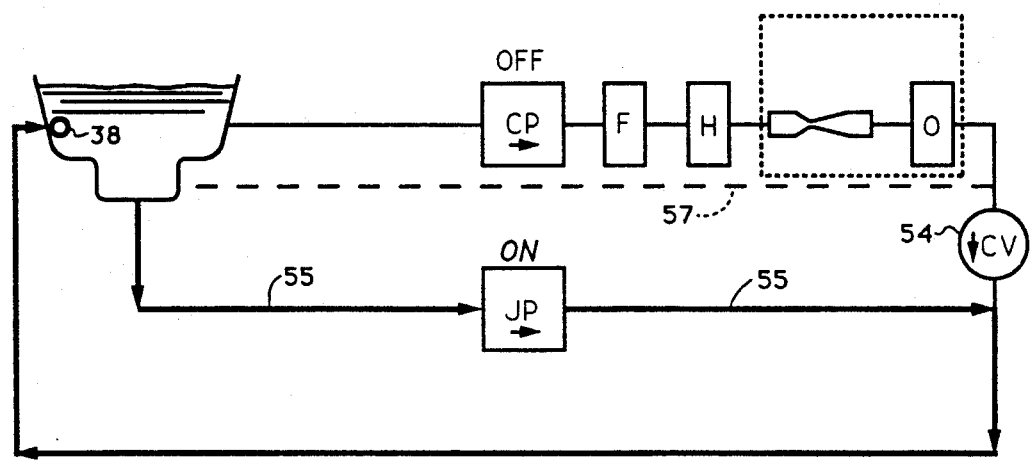
Figure 2C:
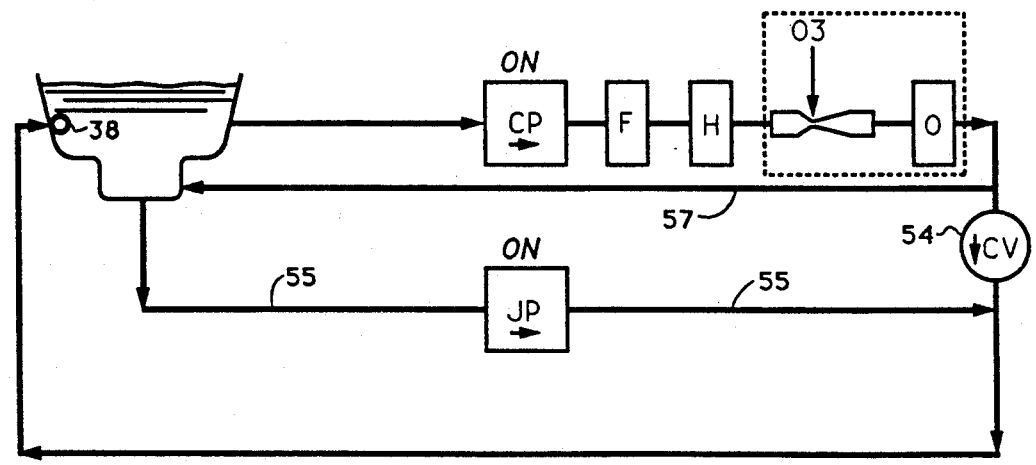

FIGS. 2a-2c are schematic views of a preferred embodiment of this invention which provides a solution to the stagnation problem of the prior art system depicted in FIG. 1a. The solution comprises a connection line 52 and check valve 54 inserted between circulation return line 26 and jet return line 36 which provides a bidirectional water conduit 55 for reverse flow through the jet pump and jet pump line when only the circulation pump is on, where the check valve prevents reverse flow through the circulation pump circuit while the jet pump is on. In FIG. 2a, with the circulation pump on and the jet pump off, the present invention provides a method of flowing water containing dissolved disinfectant through the jet pump in a direction opposite to the normal flow. The disinfectant optionally comprises ozone ("O3"), and preferably an ozone line one-way check valve (not illustrated) is included in the ozone gas line just above the ozone injection point or venturi 24. When the circulation pump is on and the jet pump off, the flow of disinfectant-containing water is split at tee 56 and flows backwards through the jet pump as well as directly to the spa. In FIG. 2b, where the jet pump is on and the circulation pump and ozone are off, the check valve 54 functions to prevent back-flow through the venturi, filter and circulation pump to insure that bacteria from the filter or from any biofilm upstream of the point of ozonation cannot contaminate the bathing tank. In FIG. 2c, with both pumps on simultaneously, the check valve 54 is closed (because the jet pump has a much higher back pressure than the circulation pump), thus serving to isolate the two loops and providing a circulation identical to that in the prior art embodiment shown in FIG. 1a. The pipeline 57 shown as dashed in FIGS. 2a and 2b is necessary only when the system must have the ability for the circulation pump and jet pump to be on at the same time (as is desirable in many commercial spas, where the circulation pump remains on continuously). When the pipeline 57 as shown in FIGS. 2a and 2b is not used, the check valve 54 could actually be located anywhere between the spa and its illustrated position, and an electrical interlock should be used to prevent both pumps from being on simultaneously.

Figure 3A:
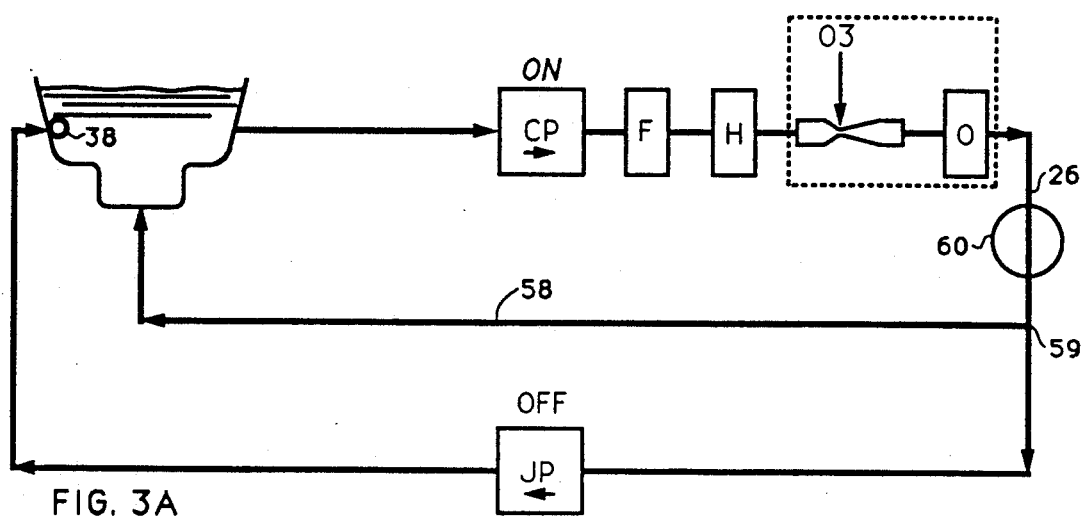
FIGS. 3a-3c are schematic views of an alternate embodiment of this invention, with a bidirectional water conduit creating reverse flow through the jet pump suction line.
Figure 3B:
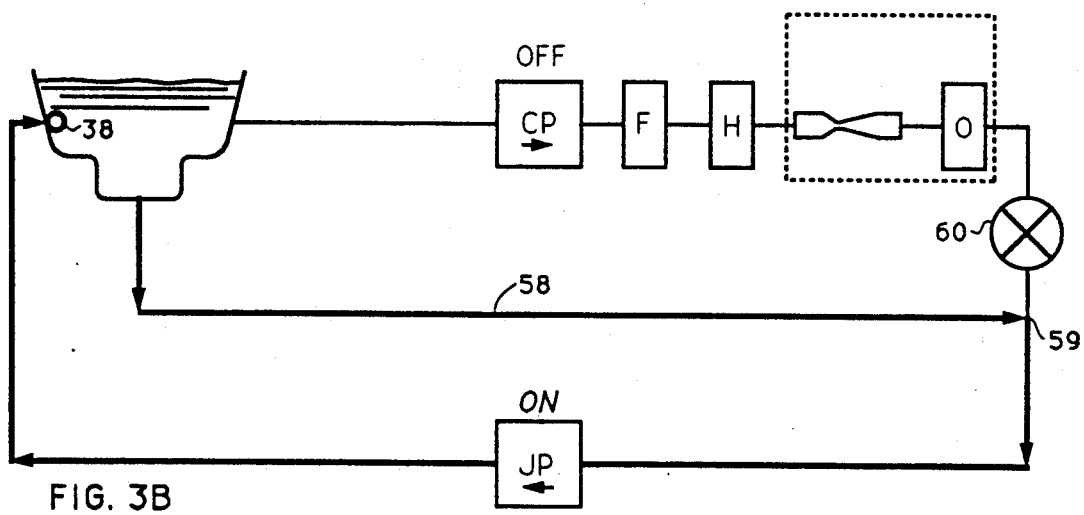
Figure 3C:
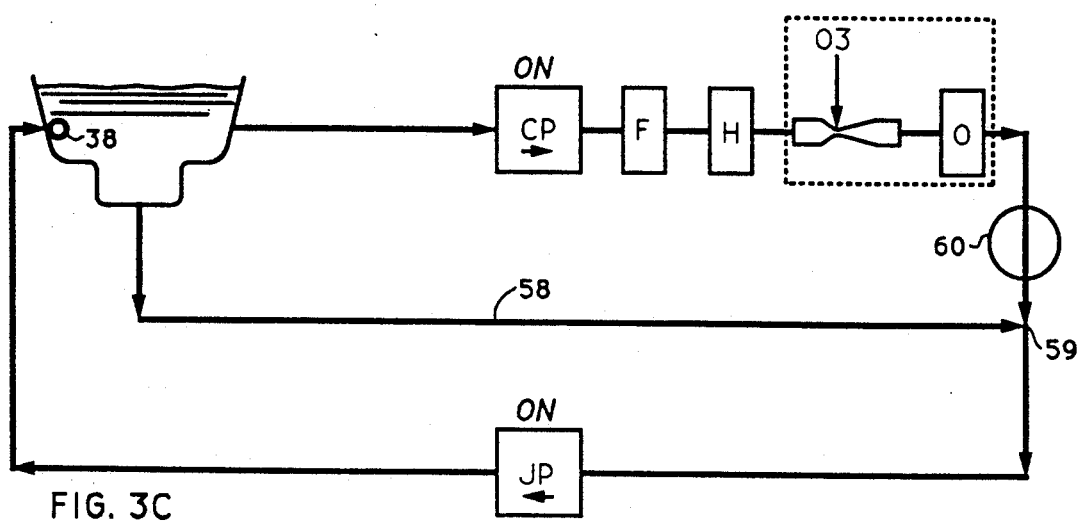

FIGS. 3a-3c are schematic views of an alternate embodiment of this invention, with a portion of the jet pump suction line serving as bidirectional water conduit 58. In this embodiment, the jet pump is positioned in the hydraulic circuit in circulation return line 26 after a tee 59, with a valve 60 upstream of the tee remaining open while the circulation pump is on. FIG. 3a shows the circulation pump on and the jet pump off, so that disinfecting water is split at the tee and flows through the jet pump as well as directly to the spa. FIG. 3b shows the circulation pump and ozone off and the jet pump on, with shut-off valve 60 closed to prevent water from flowing through the circulation line while the ozone is off and to prevent air from being drawn into the venturi. FIG. 3c shows both the circulation pump and the jet pump on, in which case the valve 60 is again open. Valve 60 is preferably an automatic valve which operates cooperatively with the pumps, being closed only when the jet pump is on alone.

Figure 4A:
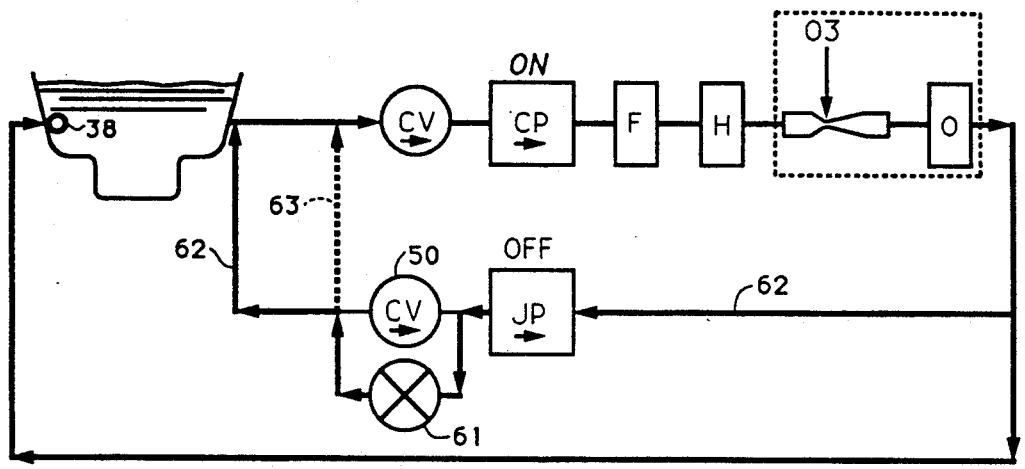
FIGS. 4a and 4b are schematic views of an additional embodiment of this invention, for spas in which the circulation pump and jet pump share a common intake from and outlet to the spa.
Figure 4B:
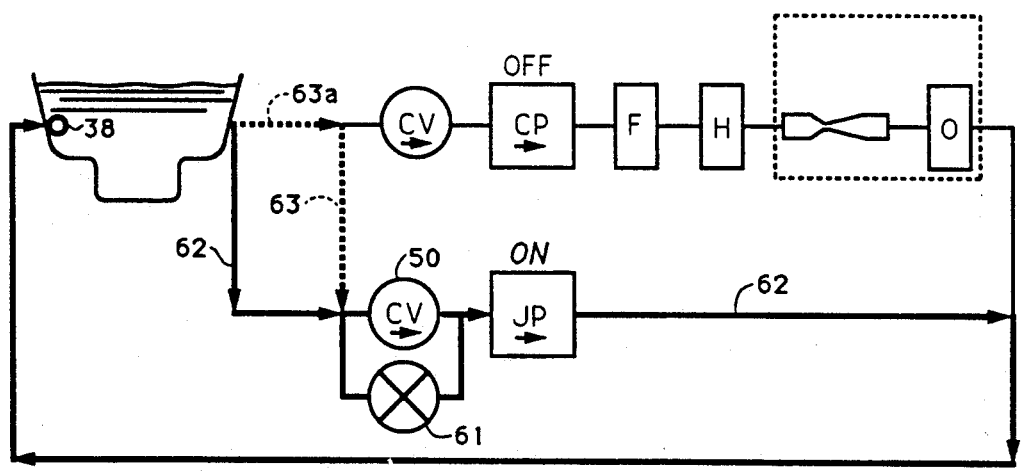

FIGS. 4a and 4b are schematic views of an additional embodiment of this invention, solving the stagnation problem for spas in which the circulation pump and jet pump share a common intake from and outlet to the spa, as was depicted in the prior art embodiment of FIG. 1b. FIG. 4a illustrates the situation when the circulation pump is on and the jet pump is off. Bypass means 61 provides a slight leak to allow a flow around check valve 50, thereby permitting some disinfectant-containing water to flow in the reverse direction through the jet pump and jet line 62. The leak should be small so that not too much water bypasses the spa. The bypass means 61 may be a section of pipe, an orifice, an adjustable valve, or a slight leak intentionally designed into check valve 50. In FIG. 4b, with the circulation pump off and the jet pump on, the jet pump operates in the normal manner. The check valves in FIGS. 4a and 4b can be relocated into the return lines of their respective pumps.

The dotted line 63 illustrates the situation where the two circuits also share a common suction line. In this case, biofilm formation in the jet pump loop would still be prevented by the reverse flow, but when the jet pump goes on it would draw shedded biofilm from the common portion of the drain line 63a (the horizontal dotted line in FIG. 4b, which never sees reverse flow or ozonation), and thus this latter case, although it would be of benefit when a halogen disinfectant is used, would not be suitable for ozone-only applications. Another embodiment of the method shown in FIGS. 4a and 4b can be obtained by moving the jet pump to the lower plumbing line and adding a shut-off valve, in analogy to the relationship of the embodiment illustrated in FIG. 3 to the embodiment illustrated in FIG. 2.

Figure 5A:
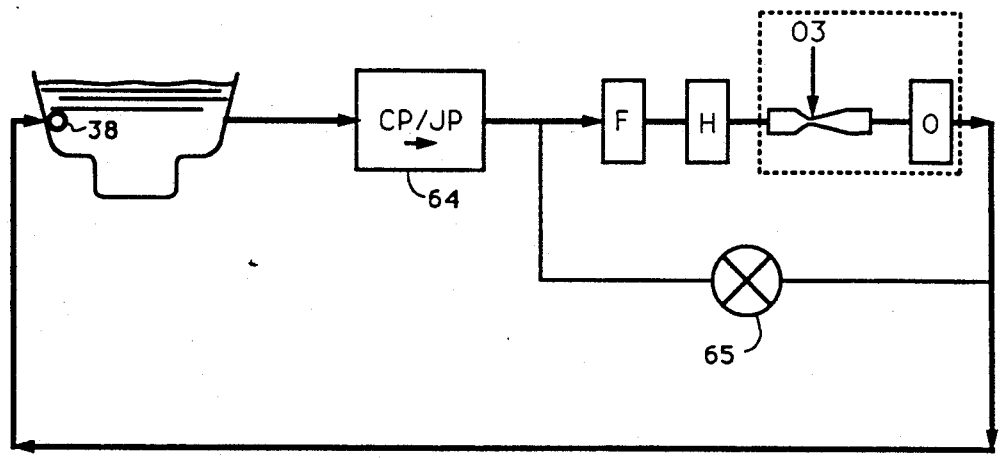
FIG. 5a is a schematic view of a prior art dual speed single pump plumbing system.
Figure 5B:
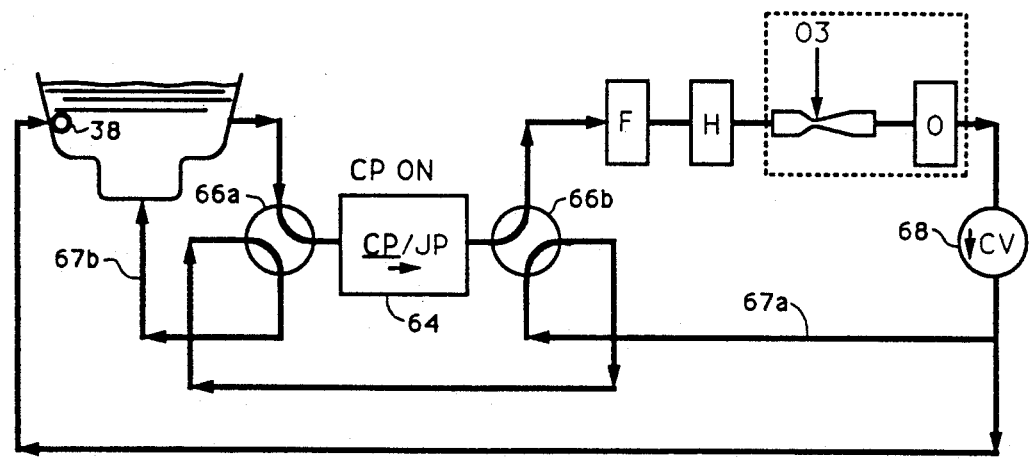
FIGS. 5b and 5c are schematic views of a dual speed single pump embodiment of this invention, employing two four-way automatic valves.
Figure 5C:
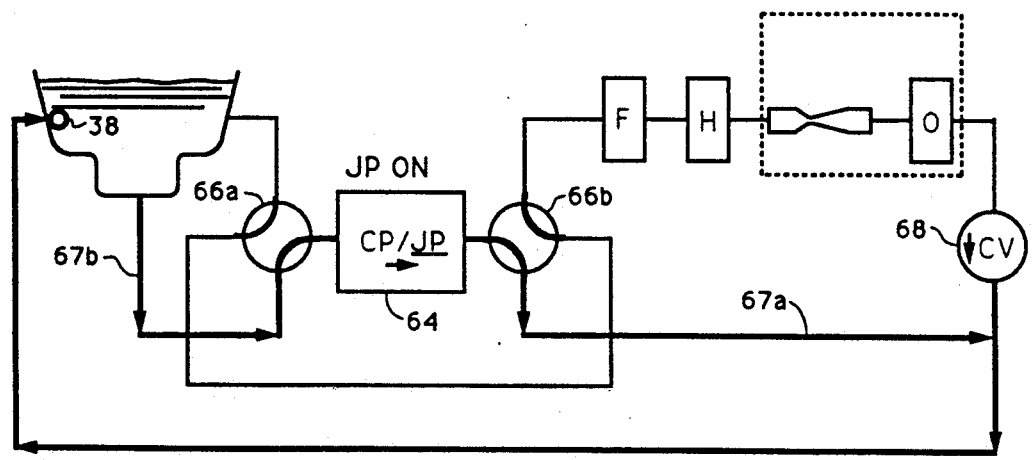

FIG. 5a is a schematic view of a prior art dual-speed pump hydraulic system which utilizes a single dual-speed pump 64 for both circulation and jet functions, and also a bypass loop including valve 65 which is closed for low speed (circulation function) and open for high speed (jet function) in order to allow the sizing of filter, heater, and ozonator components for the lower circulation flow rate. This prior art configuration allows stagnation in the bypass loop and will pump biofilm bacteria from the suction line and bypass loop into the spa when the bypass valve 65 is open. FIGS. 5b and 5c are schematic views of a single dual-speed pump embodiment of the present invention which prevents biofilm formation, employing dual-speed pump 64, two four-way automatic valves 66a, 66b, and check valve 68, with bidirectional conduits 67a and 67b serving as circulation return lines in one flow direction and as jet lines in the other flow direction. In FIG. 5b, where the low (circulation) speed is on, valves 66a and 66b are actuated so as to circulate water through both the circulation and jet circuits (analogous to the embodiment depicted in FIG. 2a). In FIG. 5c, where the high (jet) speed is on, the valves are actuated so that the jet circuit operates in the normal manner (analogous to the embodiment depicted in FIG. 2b). In this case, check valve 68 prevents reverse flow through the venturi, filter, and related components. Check valve 68 could be eliminated if at least one of the 4-way valves was asymmetrically designed in order to enable it to take over that function.

Figure 6A:
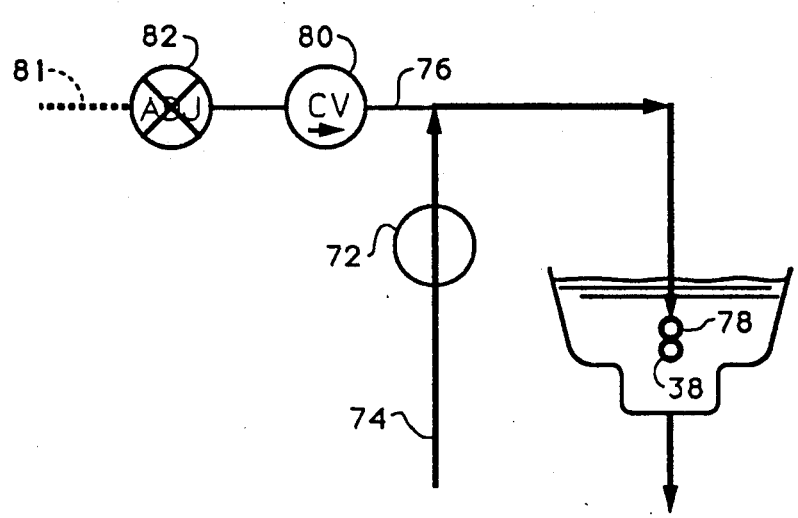
FIGS. 6a and 6b are schematic views of the automatic jet air line purge of this invention.
Figure 6B:
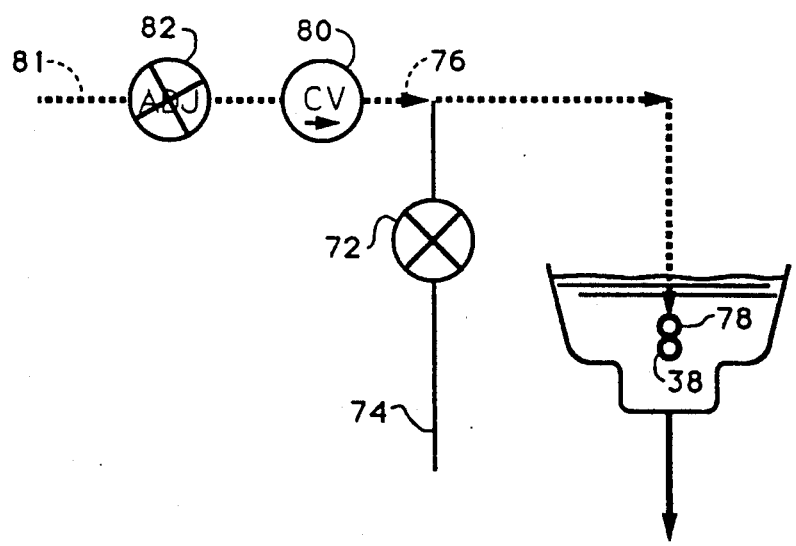

FIGS. 6a and 6b are schematic views of the automatic jet air line purge of this invention. This method enables the flowing of water containing dissolved disinfectant through the jet air lines to prevent bacterial and biofilm growth. The arrangement and use of jet air lines in the prior art puts them into the category of dead-ended pipes and blind cavities described above, since they have no through-flow of water, being filled most of the time half with stagnant water and half with air. The method of the present invention solves this biofilm problem, as shown in FIG. 6, by routing into the air lines during times that the air jets are not needed, a portion of the disinfectant-containing water returning to the spa. This prevents stagnation and keeps all of the airlines disinfected.

In FIGS. 6a and 6b, the thick solid arrows represent a flow of water, and the dotted arrows represent a flow of air. In FIG. 6a, two-way valve 72 is open, allowing disinfectant-containing water from a water line 74 to flow into air line 76, where it exits at the jet's venturi air outlet 78. Check valve 80 prevents water from escaping through air intake 81. Adjustable valve 82 is an optional manual air regulation means. In FIG. 6b, where valve 72 is closed, the system operates in the traditional manner. When the water line 74 serves as an additional return line for the circulation pump, this arrangement can provide the added benefit of a decreased back pressure on the pump, thus increasing its circulation rate while valve 72 is open.

Instead of the two-way valve and check valve shown, a single three-way valve could be substituted. In either case, the valve would be "normally open" to water flow, and could be either:

1) A normally open manual spring-wound timer valve, which upon manual actuation stops the water flow for, for example, up to thirty minutes, during which time only air sucked through the check valve is delivered to the jet, increasing the force of the jetstream in the spa, with the air flow adjustable via the manual air valve 82. After the timer runs out, for example, after thirty minutes, the water valve re-opens by itself (so that one can't defeat the water flush by forgetting to re-open it) and flushing again occurs whenever either pump is on; or 2) A normally open solenoid or water-pressure activated valve which automatically closes whenever the jet pump is on, causing only air to be sucked into the jets through the check valve. The flow of air can be manually adjustable via optional air flow valve 82.

Figure 7A:
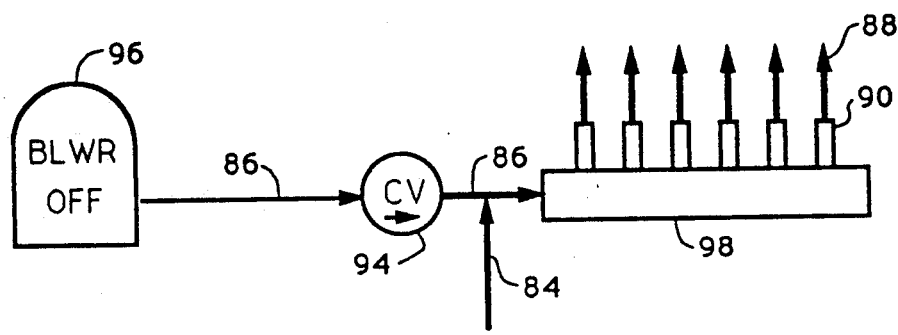
FIGS. 7a and 7b are schematic views of the automatic bubbler chamber and bubbler outlet purge of this invention.
Figure 7B:
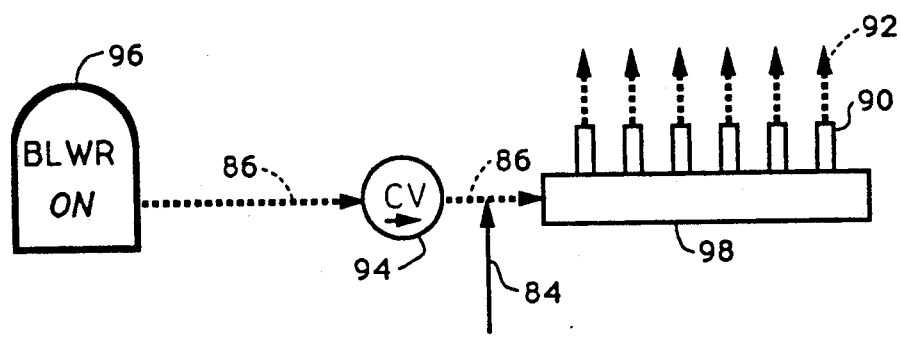

FIGS. 7a and 7b are schematic views of the automatic bubbler chamber and bubbler outlet purge of this invention. This method enables the flowing of purge water containing dissolved disinfectant through the bubbler and its outlets to prevent stagnation and biofilm growth. In FIGS. 7a and 7b the vertical arrow 84 pointing up from below represents a connecting line which connects a water circulation return line to the blower air line 86, the thick solid arrows 88 represent an outflow of water from the bubbler outlets 90, and the dotted arrows 92 represent a flow of air or a flow of a mixture of air and water. The check valve 94, traditionally present to prevent water in the spa from backing up to the bubbler's blower 96, now also serves to prevent water from connecting line 84 from backing up to the blower. This check valve is best located as close to the bubbler manifold 98 as possible, and the connecting line 84 should be installed immediately adjacent to the check valve to avoid creating a stagnant blind leg.

The blower and the circulation pump can be on at the same time. Alternatively, an electrical interlock can be used to automatically turn off the circulation pump while the blower is on, or an automatic valve can be employed to close the connecting line while the blower is on. A timer switch should be used for the blower to provide an automatic return to purging mode.

While this invention has been described in connection with preferred embodiments thereof, it is obvious that modifications and changes therein may be made by those skilled in the art to which it pertains without departing from the spirit and scope of the invention. For example, this invention is applicable to spas utilizing any disinfectant means, i.e. in spas employing ozone or chlorine or bromine or any other disinfectant, either alone or in any combination. Accordingly, the scope of this invention is to be limited only by the appended claims.

What is claimed as invention is:

1. A method for preventing biofilm growth in a spa having a hydraulic system, said hydraulic system including a circulation line having a circulation suction line, a circulation pump, a circulation return line, and means for adding a disinfectant to water in said circulation line, and further including a jet line having a jet suction line, a jet pump, and a jet return line, said method comprising:
providing a bidirectional water conduit in line with said jet pump through which water flows in one direction when only the circulation pump is on, and in the other direction when the jet pump is on, thereby flowing water containing a dissolved disinfectant from said disinfectant adding means through said bidirectional conduit to prevent water stagnation and biofilm growth in said jet line when said jet pump is off.

2. The method of claim 1 comprising:
providing a connecting line between said circulation return line and said jet return line.

3. The method of claim 2 further providing one-way valve means in said connecting line, said one-way valve means enabling flow only in the direction from said circulation return line to said jet return line.

4. The method of claim 3 wherein said one-way valve means comprises a check valve.

5. The method of claim 1 comprising:
providing a connecting line between said circulation return line and said jet suction line.

6. The method of claim 5 including valve means comprising an automatic valve operating cooperatively with said circulation pump and said jet pump so that said valve is closed when said jet pump is on and said circulation pump is off.

7. The method of claim 1 wherein said hydraulic system further includes a common circulation line/jet line intake, and said circulation line and said jet line each includes a one-way valve means, said method further comprising:
providing a bypass means around said jet line one-way valve means.

8. The method of claim 7 wherein said bypass means comprises an intentional leak in said jet line one-way valve.

9. The method of claim 1 wherein said hydraulic system has a combination circulation/jet pump, said method comprising:
providing automatic valve means for circulating water through both the circulation line and jet line while the circulation pump speed is on, and delivering water only through said jet line while the jet pump speed is on.

* * * * *